(12) United States Patent
Zhi

(10) Patent No.: US 10,435,429 B2
(45) Date of Patent: Oct. 8, 2019

(54) 5-FLUOROURIDINE MONOPHOSPHATE CYCLIC TRIESTER COMPOUNDS

(71) Applicant: NUCORION PHARMACEUTICALS, INC., San Diego, CA (US)

(72) Inventor: Lin Zhi, San Diego, CA (US)

(73) Assignee: Nucorion Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 16/144,895

(22) Filed: Sep. 27, 2018

(65) Prior Publication Data

US 2019/0100551 A1   Apr. 4, 2019

Related U.S. Application Data

(60) Provisional application No. 62/567,673, filed on Oct. 3, 2017.

(51) Int. Cl.
  *C07H 19/11* (2006.01)
  *A61P 35/00* (2006.01)
(52) U.S. Cl.
  CPC .............. *C07H 19/11* (2013.01); *A61P 35/00* (2018.01)
(58) Field of Classification Search
  None
  See application file for complete search history.

(56) References Cited

U.S. PATENT DOCUMENTS

| | | | |
|---|---|---|---|
| 4,689,404 A | 8/1987 | Kawada et al. | |
| 4,692,434 A | 9/1987 | Hertel | |
| 4,966,891 A | 10/1990 | Morio et al. | |
| 5,476,932 A | 12/1995 | Brinkman et al. | |
| 6,312,662 B1 * | 11/2001 | Erion ................ | A61K 31/7056 424/9.1 |
| 7,456,155 B2 | 11/2008 | Sommadossi et al. | |
| 8,097,706 B2 | 1/2012 | Lee et al. | |
| 8,603,999 B2 | 12/2013 | Drummond et al. | |
| 8,653,048 B2 | 2/2014 | Xue et al. | |
| 8,741,858 B2 | 6/2014 | Ren et al. | |
| 9,447,137 B2 | 9/2016 | Suo | |
| 2009/0069557 A1 | 3/2009 | Palle et al. | |
| 2009/0221524 A1 | 9/2009 | Kotra et al. | |
| 2010/0075917 A1 | 3/2010 | Decout et al. | |
| 2010/0286084 A1 | 11/2010 | Ren et al. | |
| 2011/0183933 A1 | 7/2011 | Guzi et al. | |
| 2012/0009147 A1 | 1/2012 | Cho et al. | |
| 2012/0070411 A1 | 3/2012 | Beigelman et al. | |
| 2012/0088908 A1 | 4/2012 | Xue et al. | |
| 2015/0224208 A1 | 8/2015 | Ueki et al. | |
| 2017/0057981 A1 | 3/2017 | Chen et al. | |

FOREIGN PATENT DOCUMENTS

| | | |
|---|---|---|
| CN | 1033183 A | 5/1989 |
| CN | 101525361 A | 9/2009 |
| CN | 101875680 A | 11/2010 |
| CN | 101921303 A | 12/2010 |
| CN | 102219817 A | 10/2011 |
| CN | 106554382 A | 4/2017 |
| EP | 0 588 317 A1 | 3/1994 |
| EP | 0 602 454 B1 | 4/1996 |
| EP | 2 423 215 A1 | 2/2012 |
| EP | 2 615 101 A1 | 7/2013 |
| WO | WO 02/12242 A2 | 2/2002 |
| WO | WO 2005/018330 A1 | 3/2005 |
| WO | WO 2006/065525 A1 | 6/2006 |
| WO | WO 2008/030373 A2 | 3/2008 |
| WO | WO 2008/083465 A1 | 7/2008 |
| WO | WO 2008/144980 A1 | 12/2008 |
| WO | WO 2009/082846 A1 | 7/2009 |
| WO | WO 2009/106243 A2 | 9/2009 |
| WO | WO 2010/027326 A1 | 3/2010 |
| WO | WO 2010/056403 A1 | 5/2010 |
| WO | WO 2012/031539 A1 | 3/2012 |
| WO | WO 2012/040126 A1 | 3/2012 |
| WO | WO 2013/142525 A1 | 9/2013 |
| WO | WO 2014/074725 A1 | 5/2014 |
| WO | WO 2014/124430 A1 | 8/2014 |
| WO | WO 2014/145207 A1 | 9/2014 |
| WO | WO 2015/081133 A2 | 6/2015 |
| WO | WO 2015/134334 A1 | 9/2015 |
| WO | WO 2016/138026 A1 | 9/2016 |
| WO | WO 2018/113652 A1 | 6/2018 |

OTHER PUBLICATIONS

Bentrude et al., "Efficient Preparation of Cyclc 3',5'-Phosphoramidates and Amidates of Antiviral and Antitumor 5-X-2'-Deoxyuridines (X=H, CH3, I, F, CF3, trans-CH=CHBr)," Nucleosides and Nucleotides (1989) vol. 8, No. 7, pp. 1359-1367.

Béres et al., "An Efficient Synthesis of Certain 5-Substituted-2'-Deoxyuridine 3',5'-Cyclic Monophosphate P—O-Alkyl_Aralkyl) Esters. The Crystal and Molecular Structure of 5-Iodo-2'-Deoxyuridine 3',5'-Cyclic Monophosphate P—O-methyl Ester with Axial Methoxy Group," Tetrahedron (1984) vol. 40, No. 12, pp. 2405-2414.

Chen et al., "A Facile One-Pot Synthesis of N4-Alkyloxycarbonyl Cytosine Nucleosides," Synthetic Communications (2004) vol. 34, No. 18, pp. 3273-3279.

Cheng et al., "QSAR Models for Phosphoramidate Prodrugs of 2'-Methylcytidine as Inhibitors of Hepatitis C Virus Based on PSO Boosting," Chem Biol and Drug Design (2011) 78:948-959.

Crook et al., "Examining the origin of selectivity in the reaction of racemic alcohols with chiral N-phosphoryl oxazolidinones," (2014) 25:1298-1308.

DeWaziers et al., "Cytochrome P 450 Isoenzymes, Epoxide Hydrolase and Glutathione Transferases in Rat and Human Hepatic and Extraheptaic Tissues," J Pharmacol and Experimental Therapeutics (1990) vol. 253, No. 1, pp. 387-394.

Donghi et al., "Synthesis and evaluation of novel phosphoramidate prodrugs of 2'-methyl cytidine as inhibitors of hepatitis c virus NS5B polymerase," Bioorganic & Medicinal Chem Letters (2009) 19:1392-1395.

Imai et al., "Novel cell-based reporter assay system using epitope-tagged protein for the identification of agonistic ligands of constitutive androstane receptor (CAR)," Drug Metab and Phamaco (2013) 28(4):290-298.

(Continued)

*Primary Examiner* — Traviss C McIntosh, III
(74) *Attorney, Agent, or Firm* — Knobbe, Martens, Olson & Bear, LLP

(57) ABSTRACT

Provided herein are 5-fluorouridine monophosphate cyclic triester compounds, their preparation and their uses, such as treating hepatocellular carcinoma and other types of cancer.

18 Claims, No Drawings

(56) References Cited

OTHER PUBLICATIONS

Jain et al., "Synthesis and Study of Cyclic Pronucleotides of 5-fluoro-2'-deoxyuridine," Bioorganic and Med Chem Letters (2012) vol. 22, pp. 4497-4501.

Kawaguchi et al., "Specificity of Esterases and Structure of Prodrug Esters. II. Hydrolytic Regeneration Behavior of 5-Fluro-2'-deoxyuridine (FUdR) from 3',5'-Diesters of FUdR with Rat Tissue Homogonates and Plasmain Relation to Their Antitumor Activity," Chem and Pharma Bulletin (1985) vol. 33, No. 4, pp. 1652-1659.

Lianzhi et al., "Synthesis of Acyclonucleoside Derivatives and Analogues of 5-Fluorouracil," Nanjing Yaoxueyuan Xuebao (1986) vol. 17, No. 3, pp. 161-166.

Rautio et al., "Prodrugs: design and clinical applications," Nature Reviews Drug Discovery (2008) 7:255-270.

Tanaka et al., "Chemical Synthesis of Deosyribonucleotide with a 5'-Phosphoryl Group on a Polystyrene Polymer Support by the Phosphotriester Method," Chem and Pharma Bulletin (1987) 35:2726-2733.

Thornton et al., "Nucleoside Phosphate and Phosphonate Prodrug Clinical Candidates," Journal of Medicinal Chemistry (2016) 59:10400-10410.

Zhuk, R., "Strucutre-Activity Relationship in Ftorafur (Tegafur) and Related 5-FU Prodrugs," Purine and Pyrimidine Metabolism in Man IX (1998) pp. 677-680.

Almarsson et. al., "Crystal Engineering of the Composition of Pharmaceutical Phases. Do Pharmaceutical Co-crystals Represent a New Path to Improved Medicines?" The Royal Society of Chemistry (2004) 1889-1896.

Chou et al., "Analysis of combined drug effects: a new look at a very old problem." Trends Pharmacol Sci (1983) 4:450-454.

Chou et al., "Quantitative analysis of dose-effect relationships: the combined effects of multiple drugs or enzyme inhibitors." Adv Enzyme Regul (1984) 22:27-55.

Chou, T.C., "Theoretical basis, experimental design, and computerized simulation of synergism and antagonism in drug combination studies," Pharmacol Rev. (2006) 58(3):621-81.

Kotra et al., "Structure-Activity Relationships of 2'-Deoxy-2',2'difluoro-L-erythro-pentofuranosyl Nucleosides," J Med Chem (1997) 40(1):3635-3644.

Kroep et al., "Pretreatment Deoxycytidine Kinase Levels Predict in Vivo Gemcitabine Sensitivity," Mol. Cancer Ther. (2002) 1, 371-376.

Lohman et al., "Inactivation of lactobacillus leichmannii ribonucleotide reductase by 2',2'-difluoro-2'-deoxycitifdine 5'-triphosphate: Covalent Modification," Biochem (2010) 49(7):1404-1417.

Pubchem SCHEMBLCN285547, CID: 53839260, Create Date: Dec. 4, 2011, 11 pages.

Quintiliani et al, "Design, synthesis and biological evaluation of 2'-deoxy-2',2'-diflouro-5-halouridine phosphoramidate protides," Bioorganic & Medicinal Chemistry (2011) 19(14):4338-4345.

Saiki et al. "DCK is frequently inactivated in acquired gemcitabine-resistant human cancer cells," Biochemistry and Biophysical Research Communications (2012) 421, 98-104.

Slusarczyk et al., "Application of ProTide Technology to Gemcitabine: A Successful Approach to Overcome the Key Cancer Resistance Mechanisms Leads to a New Agent (NUC-1031) in Clinical Development," J. Med. Chem. (2014) vol. 57, pp. 1531-1542.

Wilson et al., "Precursor synthesis towards the development of [1241]-labelled 2',2'-difluoro-2'deoxycytidine as a potential pet radiotracer for the anticancer drig gemcitabine," J Labelled Compounds and Radiopharmaceuticals (2001) 44(S1):S976-978.

Wu et al, "Synthesis and Biological Activity of a Gemcitabine Phosphoramidate Prodrug," J. Med Chem (2007) 50(15):3743-3746.

Zhao et al, "Synthesis and Biological Evaluation of Oral Prodrugs Based on the Structure of Gemcitabine," Chem Bio & Drug Des (2012) 80(3):479-488.

\* cited by examiner

5-FLUOROURIDINE MONOPHOSPHATE CYCLIC TRIESTER COMPOUNDS

INCORPORATION BY REFERENCE TO ANY PRIORITY APPLICATIONS

Any and all priority claims identified in the Application Data Sheet, or any correction thereto, are hereby incorporated by reference under 37 CFR 1.57. For example, this application claims priority to and the benefit of U.S. Application No. 62/567,673, filed on Oct. 3, 2017, the disclosure of which is incorporated herein in its entirety by reference.

FIELD

The present disclosure relates to the field of chemistry and medicine. More specifically, the present disclosure relates to 5-fluoro-2'-deoxyuridine and 5-fluorouridine monophosphate cyclic triester compounds, their preparation and their uses. In some embodiments, such compounds are useful to selectively deliver certain pharmaceutical agents to the liver.

BACKGROUND

The following description of the background is provided to aid in understanding the invention, but is not admitted to be, or to describe, prior art to the invention.

Natural nucleos(t)ide compounds are essential molecular building blocks of life and many nucleos(t)ide analog compounds are widely used as antiviral and anticancer agents. Due to the poor lipophilic nature, nucleos(t)ide analog compounds are rarely used as an oral agent. Nucleos(t)ide analog compounds may be used in a form to enhance their oral absorption (e.g., See P. J. Thornton, et al. Journal of Medicinal Chemistry 59:10400-10410 (2016) and J. Rautio, et al. Nature Reviews Drug Discovery 7:255-270 (2008)).

Despite the known nucleos(t)ide analog compounds, there is a need for new compounds with favorable physicochemical, biopharmaceutical or pharmacokinetic properties. For example, liver-targeting compounds which are not active outside the liver reducing pharmacological or toxicological effects of a biologically active agent outside the target tissue. Thus, there is a need for improved liver-targeting compounds in which the compounds remain relatively non-cytotoxic outside the liver.

SUMMARY

Novel 5-fluorouridine monophosphate cyclic triester compounds, their preparation and their uses are described. Some embodiments are related to novel 5-fluorouridine monophosphate cyclic triester compounds that are delivered orally to the liver where the compounds provide a therapeutic benefit. Another aspect includes the use of the 5-fluorouridine monophosphate cyclic triester compounds to treat diseases that benefit from enhanced drug distribution to the liver and like tissues and cells, including but not limited to cancer. In another aspect, the 5-fluorouridine monophosphate cyclic triester compounds are used to increase the pharmacological or clinical activity of certain classes of pharmaceutical compounds such as nucleos(t)ide analog compounds. Some additional embodiments relate to a method of making the 5-fluorouridine monophosphate cyclic triester compounds.

Some embodiments provided herein include a compound of Formula Ia or Ib:

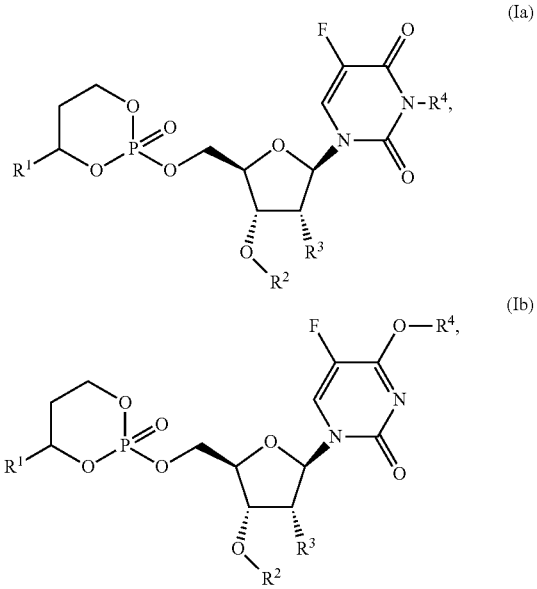

or a stereoisomer or a pharmaceutically acceptable salt thereof, wherein $R^1$, $R^2$, $R^3$, and $R^4$ have any of the values described herein.

Some embodiments relate to a pharmaceutical composition comprising any of the above compounds and a pharmaceutically acceptable excipient.

Some embodiments relate to a method of treating a disease, disorder or condition comprising administering an effective amount of any of the above compounds.

In some embodiments, the disease, disorder or condition is a disease, disorder or condition of the liver.

In some embodiments, the disease, disorder or condition is hepatocellular carcinoma.

In some embodiments, the disease, disorder or condition is other types of cancer.

In some embodiments, the non-liver disease, disorder or condition is a cancer, or other disease in which the 5-fluorouridine monophosphate cyclic triester compounds enhances the distribution of a reference drug to the target tissue or cell.

Some embodiments relate to a method of treating a liver disease comprising administering an effective amount of a compound of any of the above compounds to a subject in need thereof.

Some embodiments further comprise administering an effective amount of at least one additional therapeutic agent to the subject in need thereof.

In some embodiments, the subject is a mammal.
In some embodiments, the subject is human.
In some embodiments, the cell is in vivo.
In some embodiments, the cell is ex vivo.
In some embodiments, the cell is a hepatocyte.
In some embodiments, the cell is mammalian.
In some embodiments, the cell is human.

Some embodiments of the compounds, compositions, and methods provided herein include a pharmaceutical composition comprising any of the compounds provided herein and a pharmaceutically acceptable excipient.

Some embodiments of the compounds, compositions, and methods provided herein include a method of treating a disease or condition in the liver in a subject comprising administering an effective amount of any of the compounds provided herein to a subject in need thereof.

Some embodiments of the compounds, compositions, and methods provided herein include the use of any one of the compounds provided herein for treating a disease in the liver or a disease or condition in which the physiological or pathogenic pathways involve the liver in a subject.

Some embodiments also include the use of any one of the compounds provided herein in combination with an additional therapeutic agent(s).

Some embodiments of the compounds, compositions, and methods provided herein include any one of the compositions provided herein for use in the preparation of a medicament for treating a disease or condition in the liver.

DETAILED DESCRIPTION

5-Fluoro-2'-deoxyuridine is clinically used via intravenous injection as an anti-cancer agent to treat many types of cancers, mostly colorectal cancer. Main function of 5-fluoro-2'-deoxyuridine is to be converted to its monophosphate form that inhibits the enzyme thymidylate synthase that is essential for new cell growth. 5-Fluoro-2'-deoxyuridine can also be metabolized to 5-fluorouracil, in various metabolic active forms such as 5-fluorourindine and 5-fluoro-2'-deoxyuridine triphosphates, that can cause interference with DNA and RNA synthesis. Other forms of 5-fluorouracil have been developed and capecitabine is the only oral agent available in the market. However, the efficiency of capecitabine to deliver the actives to the target tissues is limited.

The present embodiments are directed to compositions and methods related to novel 5-fluorouridine monophosphate cyclic triester compounds, their preparation and their uses. In some embodiments, the novel 5-fluorouridine monophosphate cyclic triester compounds facilitate delivery into cells of the active form of therapeutic agents, such as nucleoside monophosphates.

These 5-fluorouridine monophosphate cyclic triester compounds and their stereoisomers and pharmaceutically acceptable salts are represented by Formula Ia or Ib:

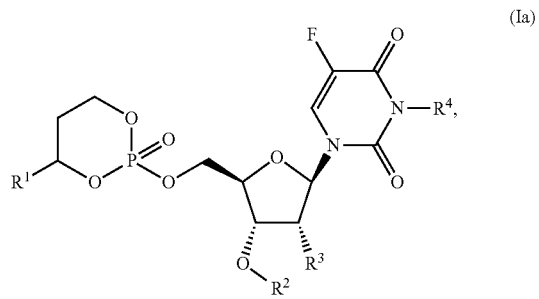

(Ia)

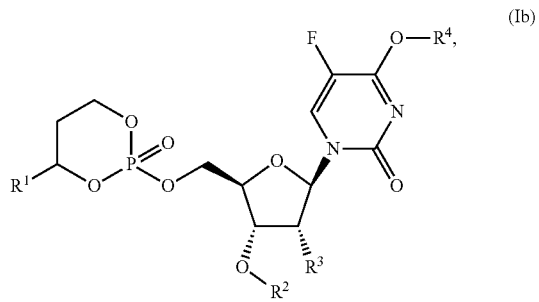

(Ib)

wherein $R^1$, $R^2$, $R^3$, and $R^4$ have any of the values described herein.

In some embodiments, $R^1$ is selected from a group of an optionally substituted aryl, and an optionally substituted heteroaryl. In some embodiments, $R^1$ is optionally substituted aryl. In some embodiments, $R^1$ is substituted phenyl. In some embodiments, $R^1$ is 3-chlorophenyl. In some embodiments, $R^1$ is substituted phenyl, $R^2$ is H, or an optionally substituted $C_1$-$C_{10}$ acyl; $R^3$ is H, or OH; and $R^4$ is H.

In some embodiments, $R^2$ is selected from a group of H, an optionally substituted $C_1$-$C_{10}$ heteroalkyl, an optionally substituted $C_1$-$C_{10}$ acyl, an optionally substituted $C_1$-$C_{10}$ heteroacyl, an optionally substituted $C_1$-$C_{10}$ alkyl-C-carboxy, and an optionally substituted $C_1$-$C_{10}$ alkyl-C-amido. In some embodiments, $R^2$ is H, or an optionally substituted $C_1$-$C_{10}$ acyl. In some embodiments, $R^2$ is —C(=O)CH$_3$, —C(=O)CH$_2$CH$_3$, —C(=O)CH$_2$CH$_2$CH$_3$, —C(=O)CH(CH$_3$)$_2$ or —C(=O)C(CH$_3$)$_3$.

In some embodiments, $R^3$ is selected from a group of H, OH, and an optionally substituted $C_1$-$C_{10}$ acyloxy. In some embodiments, $R^3$ is H, or OH. In some embodiments, $R^3$ is H.

In some embodiments, $R^4$ is selected from a group of H, an optionally substituted $C_1$-$C_{10}$ heteroalkyl, and an optionally substituted $C_1$-$C_{10}$ acyl. In some embodiments, $R^4$ is H.

Some embodiments provided herein include a compound selected from the group consisting of:

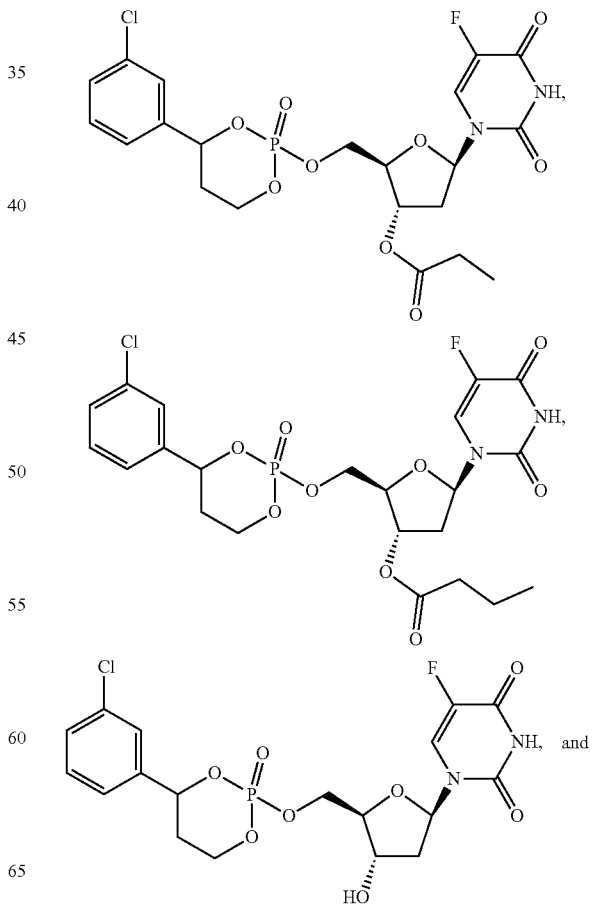

and

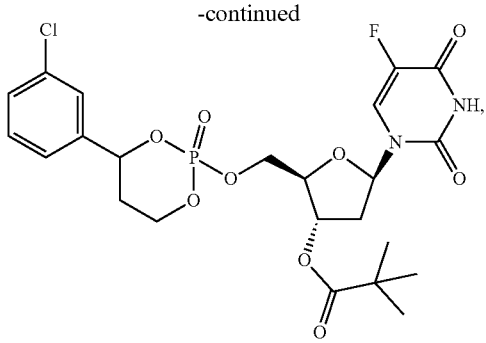

or a stereoisomer or a pharmaceutically acceptable salt thereof.

In some embodiments, the 5-fluorouridine monophosphate cyclic triester compounds of Formula Ia and Ib are substrates of liver enzymes such as cytochrome p450 isozymes CYP3As (a family of monooxygenase), dehydrogenases, esterases, and amidases.

CYP3A4 is expressed in the liver in a level much higher than other tissues (DeWaziers et al. J Pharm Exp Ther 253:387 (1990)). 5-Fluorouridine monophosphate cyclic triester compounds of Formula Ia and Ib are predominantly activated via CYP3A4 in the liver. In some embodiments, the compounds of Formula Ia and Ib have high efficiency in liver-targeting via selective delivery of biologically active agents to the liver. In some embodiments, the 5-fluorouridine monophosphate cyclic triester compounds are used to increase the therapeutic index of a reference drug, since the compounds of Formula Ia and Ib may not be active or may be less active outside the liver.

In some embodiments, due to the liver-targeting nature of the 5-fluorouridine monophosphate cyclic triester compounds of Formula Ia and Ib, the compounds are used to treat diseases that benefit from enhanced reference drug distribution to the liver and like tissues and cells, including but not limited to diseases in the liver, such as liver cancer.

In some embodiments, the disclosed compounds are used to improve pharmacokinetic properties such as prolonging half-life or enhancing absorption of a reference drug. In addition, the disclosed methodology can be used to achieve sustained delivery of an active therapeutic agent. Due to the pharmacokinetic property enhancement of the 5-fluorouridine monophosphate cyclic triester compounds of Formula Ia and Ib, the compounds are used to treat diseases that benefit from enhanced drug properties, including but not limited to diseases such as other types of cancers. In some embodiments, a method of making these compounds is described.

Certain compounds of Formula Ia and Ib have asymmetric centers where the stereochemistry may be unspecified, and the diastereomeric mixtures of these compounds are included, as well as the individual stereoisomers when referring to a compound of Formula Ia and Ib generally.

Some embodiments of the compounds, compositions and methods provided herein include a pharmaceutical composition comprising a compound provided herein and a pharmaceutically acceptable carrier.

Some embodiments also include administering an effective amount of a second or multiple therapeutic agents in combination with a compound provided herein to the subject in need thereof.

In some embodiments, the subject is mammalian.
In some embodiments, the subject is human.

Some embodiments of the compounds, compositions and methods provided herein include a method of testing a compound in a cell comprising contacting the cell with the disclosed compounds.

Some embodiments of the compounds, compositions and methods provided herein include use of a compound provided herein in the treatment of a disease in the liver.

Some embodiments include the use of a compound provided herein in combination with additional therapeutic agent(s) for the treatment of a disease in the liver.

Where the compounds disclosed herein have at least one chiral center, they may exist as individual enantiomers and diastereomers or as mixtures of such isomers, including racemates. Separation of the individual isomers or selective synthesis of the individual isomers is accomplished by application of various methods which are well known to practitioners in the art. Unless otherwise indicated, all such isomers and mixtures thereof are included in the scope of the compounds disclosed herein. Furthermore, compounds disclosed herein may exist in one or more crystalline or amorphous forms. Unless otherwise indicated, all such forms are included in the scope of the compounds disclosed herein including any polymorphic forms. In addition, some of the compounds disclosed herein may form solvates with water (i.e., hydrates) or common organic solvents. Unless otherwise indicated, such solvates are included in the scope of the compounds disclosed herein.

The skilled artisan will recognize that some structures described herein may be resonance forms or tautomers of compounds that may be fairly represented by other chemical structures, even when kinetically; the artisan recognizes that such structures may only represent a very small portion of a sample of such compound(s). Such compounds are considered within the scope of the structures depicted, though such resonance forms or tautomers are not represented herein.

Isotopes may be present in the compounds described. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

Definitions

In accordance with the present disclosure and as used herein, the following terms are defined with the following meanings, unless explicitly stated otherwise. It is to be understood that both the foregoing general description and the following detailed description are exemplary and explanatory only and are not restrictive of the subject matter claimed. In this application, the use of the singular includes the plural unless specifically stated otherwise. In this application, the use of "or" means "and/or" unless stated otherwise. Furthermore, use of the term "including" as well as other forms, such as "includes," and "included" is not limiting.

As used herein, ranges and amounts can be expressed as "about" a particular value or range. "About" also includes the exact amount. Hence "about 10%" means "about 10%" and also "10%."

As used herein, "optional" or "optionally" means that the subsequently described event or circumstance does or does not occur, and that the description includes instances where the event or circumstance occurs and instances where it does not. For example, an optionally substituted group means that the group is unsubstituted or is substituted.

As used herein, the singular forms "a," "an" and "the" include plural referents unless the context clearly dictates otherwise. Thus, for example, reference to a composition comprising "a therapeutic agent" includes compositions with one or a plurality of therapeutic agents.

As used herein, "$C_a$ to $C_b$" or "$C_{a-b}$" in which "a" and "b" are integers refer to the number of carbon atoms in the specified group. That is, the group can contain from "a" to "b", inclusive, carbon atoms. Thus, for example, a "$C_1$ to $C_4$ alkyl" or "$C_{1-4}$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 4 carbon atoms. The alkyl group may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "heteroalkyl" refers to a straight or branched hydrocarbon chain that is fully saturated (i.e., contains no double or triple bonds) replacing one or more carbon atoms with NH (or NR), S, or $SO_2$ and where one or more carbon atoms may be substituted with oxo. The heteroalkyl group may have 1 to 20 carbon atoms (whenever it appears herein, a numerical range such as "1 to 20" refers to each integer in the given range; e.g., "1 to 20 carbon atoms" means that the heteroalkyl group may consist of 1 carbon atom, 2 carbon atoms, 3 carbon atoms, etc., up to and including 20 carbon atoms, although the present definition also covers the occurrence of the term "heteroalkyl" where no numerical range is designated).

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from $C_1$-$C_6$ alkyl, $C_2$-$C_6$ alkenyl, $C_2$-$C_6$ alkynyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocycyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocycyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, $C_1$-$C_6$ alkoxy($C_1$-$C_6$)alkyl (i.e., ether), aryloxy (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$ carbocyclyloxy (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-oxy (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl-oxy (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-$C_1$-$C_6$-alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), sulfhydryl (mercapto), halo($C_1$-$C_6$)alkyl (e.g., —CF), halo($C_1$-$C_6$)alkoxy (e.g., —$OCF_3$), $C_1$-$C_6$ alkylthio, arylthio (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$ carbocyclylthio (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-thio (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl-thio (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkylthio (optionally substituted with halo, $C_1$-$C_6$alkyl, $C_1$-$C_6$ alkoxy, $C_1$-$C_6$ haloalkyl, and $C_1$-$C_6$ haloalkoxy), 3-10 membered heterocyclyl-$C_1$-$C_6$-alkylthio (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkylthio (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkylthio (optionally substituted with halo, $C_1$-$C_6$ alkyl, $C_1$-$C_6$ alkoxy, $C_1$-$C_6$ haloalkyl, and $C_1$-$C_6$ haloalkoxy), amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (=O). Wherever a group is described as "optionally substituted" that group can be substituted with the above substituents.

As used herein, "acyl" refers to —C(=O)R, wherein R is hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein. Non-limiting examples include formyl, acetyl, propanoyl, benzoyl, and acryl.

An "heteroacyl" refers to —C(=O)R, wherein R is a $C_{1-6}$ heteroalkyl.

An "alkyloxymethylene" refers to —$CH_2OR$, wherein R is a $C_{1-6}$ alkyl, or heteroalkyl, all optionally substituted.

An "O-carboxy" group refers to a "—OC(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

A "C-carboxy" group refers to a "—C(=O)OR" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein. A non-limiting example includes carboxyl (i.e., —C(=O)OH).

A "cyano" group refers to a "—CN" group.

A "cyanato" group refers to an "—OCN" group.

An "isocyanato" group refers to a "—NCO" group.

A "thiocyanato" group refers to a "—SCN" group.

An "isothiocyanato" group refers to an "—NCS" group.

A "sulfinyl" group refers to an "—S(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

A "sulfonyl" group refers to an "—SO$_2$R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "S-sulfonamido" group refers to a "—SO$_2$NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "N-sulfonamido" group refers to a "—N(R$_A$)SO$_2$R$_B$" group in which R$_A$ and R$_b$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "O-carbamyl" group refers to a "—OC(=O)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "N-carbamyl" group refers to an "—N(R$_A$)C(=O)OR$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "O-thiocarbamyl" group refers to a "—OC(=S)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "N-thiocarbamyl" group refers to an "—N(R$_A$)C(=S)OR$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

A "C-amido" group refers to a "—C(=O)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein each optionally substituted with one or more substituents selected from the group consisting of —OH, $C_{1-6}$ alkyl, $C_{3-7}$ carbocyclyl, $C_{6-10}$ aryl, 5-10 membered heteroaryl, 3-10 membered heterocycyl, $C_{1-6}$ alkyl optionally substituted with $C_{1-6}$ alkoxy or —OH and $C_{1-6}$ alkoxy optionally substituted with $C_{1-6}$ alkoxy or —OH.

An "N-amido" group refers to a "—N(R$_A$)C(=O)R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein each optionally substituted with one or more substituents selected from the group consisting of —OH, $C_{1-6}$ alkyl, $C_{3-7}$ carbocyclyl, $C_{6-10}$ aryl, 5-10 membered heteroaryl, 3-10 membered heterocycyl, $C_{1-6}$ alkyl optionally substituted with $C_{1-6}$ alkoxy or —OH and $C_{1-6}$ alkoxy optionally substituted with $C_{1-6}$ alkoxy or —OH.

An "amino" group refers to a "—NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein. A non-limiting example includes free amino (i.e., —NH$_2$).

An "aminoalkyl" group refers to an amino group connected via an alkylene group.

An "alkoxyalkyl" group refers to an alkoxy group connected via an alkylene group, such as a "$C_{2-8}$ alkoxyalkyl" and the like.

The term "acyloxy" refers to —OC(O)R where R is alkyl.

The term "alkoxy" or "alkyloxy" refers to OR where R is alkyl, or heteroalkyl, all optionally substituted.

The term "carboxyl" refers to a C(O)OH.

The term "oxo" refers to an =O group.

The term "halogen" or "halo" refers to F (fluoro), Cl (chloro), Br (bromo) and I (iodo).

The term "haloalkyl" refer to alkyl groups containing at least one halogen, in a further aspect are 1 to 3 haloatoms. Suitable haloatoms include F, Cl, and Br.

The term "haloacyl" refer to —C(O)-haloalkyl groups.

The term "alkenyl" refers to unsaturated groups which have 2 to 12 atoms and contain at least one carbon carbon double bond and includes straight chain, branched chain and cyclic groups. Alkenyl groups may be optionally substituted. Suitable alkenyl groups include allyl.

The term "alkynyl" refers to unsaturated groups which have 2 to 12 atoms and contain at least one carbon carbon triple bond and includes straight chain, branched chain and cyclic groups. Alkynyl groups may be optionally substituted. Suitable alkynyl groups include ethynyl.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some embodiments, the aryl group has 6 to 10 carbon atoms. The aryl group may be designated as "$C_{6-10}$ aryl," "$C_6$ or $C_{10}$ aryl," or similar designations. Examples of aryl groups include, but are not limited to, phenyl, naphthyl, azulenyl, and anthracenyl.

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-7 membered heteroaryl," "5-10 membered heteroaryl," or similar designations. Heteroaryl groups may be optionally substituted. Examples of heteroaryl groups include, but are not limited to, aromatic C3-8 heterocyclic groups comprising one oxygen or sulfur atom or up to four nitrogen atoms, or a combination of one oxygen or sulfur atom and up to two nitrogen atoms, and their substituted as well as benzo- and pyrido-fused cyclic triesters, for example, connected via one of the ring-forming carbon atoms. In some embodiments, heteroaryl groups are optionally substituted with one or more substituents, independently selected from halo, hydroxy, amino, cyano, nitro, alkylamido, acyl, $C_{1-6}$-alkoxy, $C_{1-6}$-alkyl, $C_{1-6}$-hydroxyalkyl, $C_{1-6}$-aminoalkyl, $C_{1-6}$-alkylamino, alkylsulfenyl, alkylsulfinyl, alkylsulfonyl, sulfamoyl, or trifluoromethyl. Examples of heteroaryl groups include, but are not limited to, unsubstituted and mono- or di-substituted cyclic triesters of furan, benzofuran, thiophene, benzothiophene, pyrrole, pyridine, indole, oxazole, benzoxazole, isoxazole, benzisoxazole, thiazole, benzothiazole, isothiazole, imidazole, benzimidazole, pyrazole, indazole, tetrazole, quinoline, isoquinoline, pyridazine, pyrimidine, purine and pyrazine, furazan, 1,2,3-oxadiazole, 1,2,3-thiadiazole, 1,2,4-thiadiazole, triazole, benzotriazole, pteridine, phenoxazole, oxadiazole, benzopyrazole, quinolizine, cinnoline, phthalazine, quinazoline, and quinoxaline. In some embodiments, the substituents are halo, hydroxy, cyano, O—$C_{1-6}$-alkyl, $C_{1-6}$-alkyl, hydroxy-$C_{1-6}$-alkyl, and amino-$C_{1-6}$-alkyl.

As used herein, "cycloalkyl" means a fully saturated carbocyclyl ring or ring system. Examples include cyclopropyl, cyclobutyl, cyclopentyl, and cyclohexyl. The cycloalkyl group may have 3 to 10 carbon atoms (whenever it appears herein, a numerical range such as "3 to 10" refers to each integer in the given range. The cycloalkyl group may be designated as "$C_3$-$C_8$ cycloalkyl" or similar designations. By way of example only, "$C_3$-$C_8$ cycloalkyl" indicates that there are three to eight carbon atoms in the carbocyclyl ring or ring system.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations. In preferred six membered monocyclic heterocyclyls, the heteroatom(s) are selected from one up to three of O (oxygen), N (nitrogen) or S (sulfur), and in preferred five membered monocyclic heterocyclyls, the heteroatom(s) are selected from one or two heteroatoms selected from O (oxygen), N (nitrogen) or S (sulfur). Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidinyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —$CH_2$—, —$CH_2CH_2$—, —$CH_2CH(CH_3)CH_2$—, and the like. Other radical naming conventions clearly indicate that the radical is a di-radical such as "alkylene" or "alkenylene."

When two R groups are said to form a ring (e.g., a carbocyclyl, heterocyclyl, aryl, or heteroaryl ring) "together with the atoms to which they are attached," it is meant that the collective unit of the atoms and the two R groups are the recited ring. The ring is not otherwise limited by the definition of each R group when taken individually. For example, when the following substructure is present:

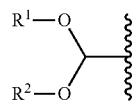

and $R^1$ and $R^2$ are defined as selected from the group consisting of alkyl and aryl, or $R^1$ and $R^2$ together with the oxygen to which they are each attached form a heterocyclyl, it is meant that $R^1$ and $R^2$ can be selected from alkyl or aryl, or alternatively, the substructure has structure:

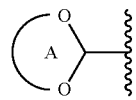

where ring A is a heterocyclic ring containing the depicted oxygens.

Similarly, when two "adjacent" R groups are said to form a ring "together with the atom to which they are attached," it is meant that the collective unit of the atoms, intervening bonds, and the two R groups are the recited ring. For example, when the following substructure is present:

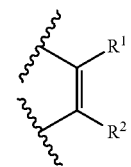

and $R^1$ and $R^2$ are defined as selected from the group consisting of hydrogen and alkyl, or $R^1$ and $R^2$ together with the atoms to which they are attached form an aryl or carbocylyl, it is meant that $R^1$ and $R^2$ can be selected from hydrogen or alkyl, or alternatively, the substructure has structure:

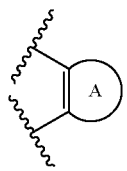

where A is an aryl ring or a carbocylyl containing the depicted double bond.

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

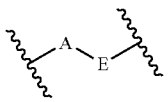

includes the substituent being oriented such that the A is attached at the leftmost attachment point of the molecule as well as the case in which A is attached at the rightmost attachment point of the molecule.

The phrase "therapeutically effective amount" means an amount of a compound or a combination of compounds that partially or fully ameliorates, attenuates or eliminates one or more of the symptoms of a particular disease or condition or prevents, modifies, or delays the onset of one or more of the symptoms of a particular disease or condition. Such amount can be administered as a single dosage or can be administered according to a regimen, whereby it is effective. Repeated administration may be needed to achieve a desired result (e.g., treatment of the disease and/or condition).

The term "pharmaceutically acceptable salt" includes salts of compounds of Formula Ia and Ib derived from the combination of a compound of the present embodiments and an organic or inorganic acid or base. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, adipic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, benzenesulfonic acid, methanesulfonic acid, ethanesulfonic acid, p-toluenesulfonic acid, (+)-7,7-dimethyl-2-oxobicyclo [2.2.1]heptane-1-methanesulfonic acid, 1,2-ethanedisulfonic acid, dodecyl sulfonic acid, salicylic acid, glucoheptonic acid, gluconic acid, glucuronic acid, hippuric acid, hydrochloride hemiethanolic acid, 2-hydroxyethanesulfonic acid, lactic acid, lactobionic acid, methylbromide acid, methyl sulfuric acid, 2-naphthalenesulfonic acid, oleic acid, 4,4'-methylenebis-[3-hydroxy-2-naphthalenecarboxylic acid], polygalacturonic acid, stearic acid, sulfosalicylic acid, tannic acid, terphthalic acid and the like. Inorganic bases from which salts can be derived include, for example, bases that contain sodium, potassium, lithium, ammonium, calcium, magnesium, iron, zinc, copper, manganese, aluminum, and the like; particularly preferred are the ammonium, potassium, sodium, calcium and magnesium salts. In some embodiments, treatment of the compounds disclosed herein with an inorganic base results in loss of a labile hydrogen from the compound to afford the salt form including an inorganic cation such as $Li^+$, $Na^+$, $K^+$, $Mg^{2+}$ and $Ca^{2+}$ and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine.

Where the number of any given substituent is not specified (e.g., "haloalkyl"), there may be one or more substituents present. For example, "haloalkyl" can include one or more of the same or different halogens. For example, "haloalkyl" includes each of the substituents $CF_3$, $CHF_2$ and $CH_2F$.

The term "patient" refers to an animal being treated including a mammal, such as a dog, a cat, a cow, a horse, a sheep, and a human. In some embodiments, the patient is a mammal, either male or female. In some embodiments, the patient is a male or female human.

The monophosphate cyclic triester compounds disclosed herein, when administered to a biological system, may generate a biologically active compound as a result of spontaneous chemical reaction(s), enzyme catalyzed chemical reaction(s), and/or metabolic chemical reaction(s), or a combination of each. The monophosphate cyclic triester compounds disclosed herein may undergo some form of a chemical transformation to produce the compound that is biologically active or is a precursor of the biologically active compound. The monophosphate cyclic triester compounds disclosed herein may be utilized, for example, to improve bioavailability, improve subject acceptability such as by masking or reducing unpleasant characteristics such as bitter taste or gastrointestinal irritability, alter solubility such as for intravenous use, provide for prolonged or sustained release or delivery, improve ease of formulation, or provide site specific delivery of the compound.

The term "stereoisomer" refers to the relative or absolute spatial relationship of the R group(s) attached to the stereogenic centers either carbon or phosphorus atoms, and refers to individual or any combination of the individual isomers such as a racemic mixture and a diastereomeric mixture. When a compound has two stereogenic centers, there are 4 potential stereoisomers.

The term "liver" refers to the liver organ.

The term "liver specificity" refers to the ratio:

[drug or a drug metabolite in liver tissue]/[drug or a drug metabolite in blood or another tissue]
as measured in animals treated with the drug or a compound as disclosed and described herein. The ratio can be determined by measuring tissue levels at a specific time or may represent an AUC (area under a curve) based on values measured at three or more time points.

The term "increased or enhanced liver specificity" refers to an increase in liver specificity ratio in animals treated with a compound as disclosed and described herein relative to animals treated with the reference drug.

The term "enhanced oral bioavailability" refers to an increase of at least about 50% of the absorption of the dose of the reference drug. In an additional aspect, the increase in oral bioavailability of the compound (compared to the reference drug) is at least about 100%, or a doubling of the absorption. Measurement of oral bioavailability usually refers to measurements of the compound as disclosed and described herein, reference drug, or drug metabolite in blood, plasma, tissues, or urine following oral administration compared to measurements following parenteral administration.

The term "therapeutic index" refers to the ratio of the dose of a reference drug or compound as disclosed and described herein that produces a therapeutically beneficial response relative to the dose that produces an undesired response such as death, an elevation of markers that are indicative of toxicity, and/or pharmacological side effects.

The term "sustained delivery" refers to an increase in the period in which there is a prolongation of therapeutically-effective reference drug levels due to the presence of the compound as disclosed and described herein.

The terms "treating" or "treatment" of a disease includes inhibiting the disease (slowing or arresting or partially arresting its development), preventing the disease, providing relief from the symptoms or side effects of the disease (including palliative treatment), and/or relieving the disease (causing regression of the disease).

The terms "molecular pathway" refers to a series of molecular events in tissues such as a receptor modulating sequence, an enzyme modulating sequence, or a biosynthesis sequence that is involved in physiological or pathophysiological functions of a living animal.

Administration and Pharmaceutical Compositions

The disclosed compounds may be used alone or in combination with other treatments. These compounds, when used in combination with other agents, may be administered as a daily dose or an appropriate fraction of the daily dose (e.g., bid). The compounds may be administered after a course of treatment by another agent, during a course of therapy with another agent, administered as part of a therapeutic regimen, or may be administered prior to therapy with another agent in a treatment program.

Examples of pharmaceutically acceptable salts include acetate, adipate, besylate, bromide, camsylate, chloride, citrate, edisylate, estolate, fumarate, gluceptate, gluconate, glucuronate, hippurate, hyclate, hydrobromide, hydrochloride, iodide, isethionate, lactate, lactobionate, maleate, mesylate, methylbromide, methylsulfate, napsylate, nitrate, oleate, palmoate, phosphate, polygalacturonate, stearate, succinate, sulfate, sulfosalicylate, tannate, tartrate, terphthalate, tosylate, and triethiodide.

Compositions containing the active ingredient may be in any form suitable for the intended method of administration. In some embodiments, the compounds of a method and/or composition described herein can be provided via oral administration, rectal administration, transmucosal administration, intestinal administration, enteral administration, topical administration, transdermal administration, intrathecal administration, intraventricular administration, intraperitoneal administration, intranasal administration, intraocular administration and/or parenteral administration.

When the compounds are administered via oral administration, for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient can be mixed with an inert solid diluent, for example calcium phosphate or kaolin, or as soft gelatin capsules wherein the active ingredient can be mixed with water or an oil medium, such as peanut oil, liquid paraffin or olive oil.

Formulations suitable for parenteral administration include aqueous and non-aqueous isotonic sterile injection solutions which may contain, for example, antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Injection solutions and suspensions may be prepared from sterile powders, granules and tablets of the kind previously described.

In some embodiments unit dosage formulations contain a daily dose or unit, daily sub-dose, or an appropriate fraction thereof, of a drug. It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those skilled in the art.

The actual dose of the compounds described herein depends on the specific compound, and on the condition to be treated; the selection of the appropriate dose is well within the knowledge of the skilled artisan. In some embodiments, a daily dose may be from about 0.1 mg/kg to about 100 mg/kg or more of body weight, from about 0.25 mg/kg or less to about 50 mg/kg from about 0.5 mg/kg or less to about 25 mg/kg, from about 1.0 mg/kg to about 10 mg/kg of body weight. Thus, for administration to a 70 kg person, the dosage range would be from about 7 mg per day to about 7000 mg per day, from about 35 mg per day or less to about 2000 mg per day or more, from about 70 mg per day to about 1000 mg per day.

Methods of Treatment

Some embodiments of the present invention include methods of treating hepatocellular carcinoma and other types of cancer. Some methods include administering a compound, composition, pharmaceutical composition described herein to a subject in need thereof. In some embodiments, a subject can be an animal, e.g., a mammal, a human. In some embodiments, the subject is a human.

Further embodiments include administering a combination of compounds to a subject in need thereof. A combination can include a compound, composition, pharmaceutical composition described herein with an additional medicament.

Some embodiments include co-administering a compound, composition, and/or pharmaceutical composition described herein, with an additional medicament or additional therapeutic agent(s). By "co-administration," it is meant that the two or more agents may be found in the patient's bloodstream at the same time, regardless of when or how they are actually administered. In one embodiment, the agents are administered simultaneously. In one such embodiment, administration in combination is accomplished by combining the agents in a single dosage form. In another embodiment, the agents are administered sequentially. In one embodiment, the agents are administered through the same route, such as orally. In another embodiment, the agents are administered through different routes, such as one being administered orally and another being administered i.v.

In some embodiments, the additional therapeutic agent for HCC treatment may be one or more of sorafenib, regorafenib, an immune-oncology agent such as a PD-1 or PD-L1 checkpoint inhibitor.

To further illustrate this invention, the following examples are included. The examples should not, of course, be construed as specifically limiting the invention. Variations of these examples within the scope of the claims are within the purview of one skilled in the art and are considered to fall within the scope of the invention as described, and claimed herein. The reader will recognize that the skilled artisan, armed with the present disclosure, and skill in the art is able to prepare and use the invention without exhaustive examples.

Synthesis of Compounds

The following procedures for the preparation of the new compounds illustrate the general procedures used to prepare the 5-fluorouridine monophosphate cyclic triester compounds. A protecting group can be introduced at different stages of synthesis of a drug. In some embodiments, they are introduced at a later stage, because of the general sensitivity of these groups to various reaction conditions. Optically pure compounds containing a single isomer at the phosphorus center can be made, for example, by separation of the diastereomers by a combination of column chromatography and/or crystallization, or by enantioselective synthesis of chiral activated phosph(on)ate intermediates.

Scheme I describes general strategies of synthesis of the 5-fluoro-2'-deoxyuridine cyclic triester compounds of Formula Ia. Treatment of the nucleoside compound of structure 1 with either alkylation or acylation agents of structures 2 and 3 provides the alkylated or acylated nucleosides of structure 4. Coupling reaction of the intermediates of structure 4 with a known phosphate compound of structures 5 or 6 yields the final product of structure 5.

Scheme I

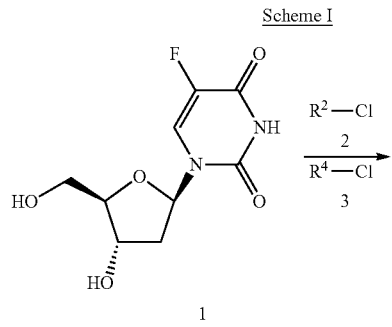

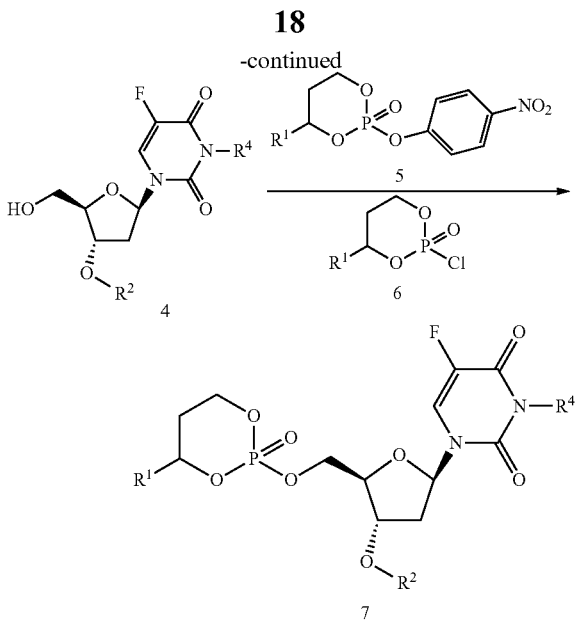

EXAMPLES

Some compounds of Formula Ia are outlined below.

Example 1

(2R,3S,5R)-2-(((4-(3-Chlorophenyl)-2-oxido-1,3,2-dioxaphosphinan-2-yl)oxy)methyl)-5-(5-fluoro-2,4-dioxo-3,4-dihydropyrimidin-1(2H)-yl)tetrahydrofuran-3-yl propionate (Compound 101)

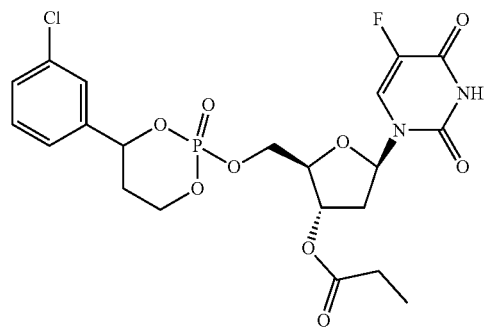 [SMILES: CCC(=O)O[C@H]1C[C@H](n2cc(F)c(=O)[nH]c2=O)O[C@@H]1COP1(=O)OCCC(c2cccc(Cl)c2)O1]

Compound 101 was prepared according to Scheme I from propionic anhydride, 1-(3-chlorophenyl)-1,3-propanediol, and 5-fluoro-2'-deoxyuridine as follows.

To an anhydrous 5-fluoro-2'-deoxyuridine (10 g, 40.6 mmol, 1.0 eq) solution in pyridine (70 mL) was added DMTrCl (15 g, 44.7 mmol, 1.1 eq) and the reaction mixture was stirred at 20° C. for 16 h monitored by TLC (DCM/MeOH=10/1, $R_f$=0.50). The reaction was quenched by MeOH (30 mL) and then concentrated under reduced pressure. The residue was extracted with EtOAc and the combined organic layers were washed with saturated NaHCO$_3$ (300 mL) and brine (200 mL), dried over Na$_2$SO$_4$, filtered and concentrated under reduced pressure to give a crude mixture. Silica gel column chromatography (petroleum ether/ethyl acetate=5/1, DCM/MeOH=40/1, 30/1) provided dimethoxytrityl alkylated product as a white solid (18 g, 33 mmol). $^1$H-NMR (400 MHz, DMSO-d$_6$) 7.86 (d, J=6.8, 1H), 7.40-7.35 (m, 2H), 7.32-7.18 (m, 7H), 6.87 (d, J=8.2, 4H), 6.15-6.10 (m, 1H), 5.73 (s, 1H), 4.29-4.22 (m, 1H), 3.91-3.83 (m, 1H), 3.72 (s, 6H), 3.25 (dd, J=5.6, 10.4, 1H), 3.13 (dd, J=2.8, 10.4, 1H), 2.29-2.10 (m, 2H).

To a solution of above compound (12 g, 21 mmol) in pyridine (77 mL) was added propionic anhydride (11 g, 84 mmol, 4.0 eq) and the reaction mixture was then stirred at 20° C. for 16 h monitored by TLC. The reaction was concentrated under reduced pressure and purified by column chromatography ($SiO_2$, petroleum ether/ethyl acetate=5/1, 3/1, DCM/MeOH=20/1) to give the propionate product (11 g, 18 mmol) as a white solid. $^1$H-NMR (400 MHz, DMSO-$d_6$) 11.90 (s, 1H), 7.92 (d, J=6.8, 1H), 7.41-7.35 (m, 2H), 7.34-7.20 (m, 7H), 6.88 (dd, J=1.2, 8.8, 4H), 6.14 (t, J=6.4 Hz, 1H), 5.25-5.19 (m, 1H), 4.09-4.04 (m, 1H), 3.74 (s, 6H), 3.37 (dd, J=5.4, 10.4, 1H), 3.19 (dd, J=3.0, 10.4, 1H), 2.47-2.42 (m, 1H), 2.39-2.28 (m, 3H), and 1.04-0.98 (m, 3H).

To a solution of above compound (6.0 g, 9.9 mmol, 1.00 eq) in DCM (60 mL) was added TFA (5.5 g, 48 mmol, 4.9 eq) and the mixture was stirred at room temperature for half hour. Standard workup followed by silica gel chromatograph yielded the dimethoxytrityl de-protected product as a pink solid (2.0 g, 6.6 mmol). $^1$H-NMR (400 MHz, DMSO-$d_6$) 11.86 (d, J=4.8, 1H), 8.21 (d, J=6.8, 1H), 6.19-6.12 (m, 1H), 5.31 (s, 1H), 5.26-5.19 (m, 1H), 4.04-3.96 (m, 1H), 3.64 (d, J=2.4, 2H), 2.40-2.32 (m, 2H), 2.30-2.24 (m, 2H), 1.04 (t, J=7.5, 3H).

To a solution of 4-(3-chlorophenyl)-2-(4-nitrophenoxy)-1,3,2-dioxaphosphinane 2-oxide (100 mg, 331 µmol) in DMF (4 mL) at −20° C. under dry nitrogen was added t-BuMgCl (1 M, 1.6 mL, 5.0 eq) and the reaction mixture was then stirred at −20° C. for 0.5 h. Above 5-fluoro-2'-deoxyuridine propionate (188 mg, 509 µmol, 1.5 eq) was added in one portion to the reaction mixture. The reaction was quenched after stirring at 20° C. for 16 h with saturated aqueous $NH_4Cl$ (20 mL), extracted with EtOAc (8 mL×3). The combined organic layers were washed with brine (20 mL), dried over $Na_2SO_4$, filtered, concentrated under reduced pressure, and purified by prep-HPLC to afford Compound 101 (100 mg, 185 µmol) as a 1:1 mixture of two diastereomers as a light-yellow solid. $^1$H-NMR (400 MHz, MeOD) 7.77 (dd, J=6.8, 8.8, 1H), 7.51-7.31 (m, 4H), 6.32-6.14 (m, 1H), 5.73 (d, J=10.8, 1H), 5.31 (d, J=2.4, 1H), 4.76-4.64 (m, 1H), 4.62-4.41 (m, 3H), 4.25 (d, J=2.4, 1H), 2.52-2.16 (m, 6H), 1.16-1.10 (m, 3H).

Example 2

(2R,3S,5R)-2-(((4-(3-Chlorophenyl)-2-oxido-1,3,2-dioxaphosphinan-2-yl)oxy)methyl)-5-(5-fluoro-2,4-dioxo-3,4-dihydropyrimidin-1(2H)-yl)tetrahydrofuran-3-yl butyrate (Compound 102)

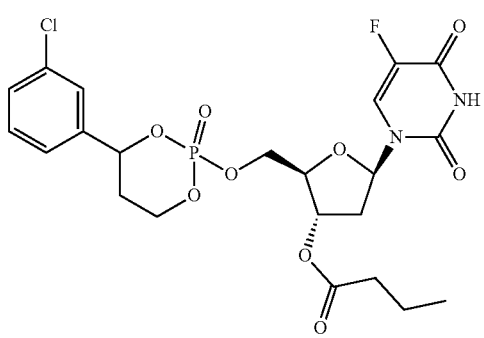 [SMILES: CCCC(=O)O[C@H]1C[C@H](n2cc(F)c(=O)[nH]c2=O)O[C@@H]1COP1(=O)OCCC(c2cccc(Cl)c2)O1]

Compound 102 can be prepared according to the method similar to that described in Example 1 from butanoic acid, 1-(3-chlorophenyl)-1,3-propanediol, and 5-fluoro-2'-deoxyuridine.

Example 3

1-((2R,4S,5R)-5-(((4-(3-Chlorophenyl)-2-oxido-1,3,2-dioxaphosphinan-2-yl)oxy)methyl)-4-hydroxytetrahydrofuran-2-yl)-5-fluoropyrimidine-2,4(1H,3H)-dione (Compound 103)

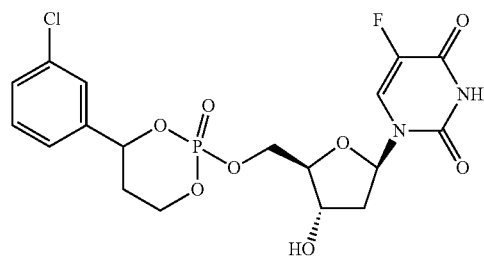 [SMILES: O=c1[nH]c(=O)n([C@H]2C[C@H](O)[C@@H](COP3(=O)OCCC(c4cccc(Cl)c4)O3)O2)cc1F]

Compound 103 was prepared according to the method similar to that described in Example 1 from 1-(3-chlorophenyl)-1,3-propanediol, and 5-fluoro-2'-deoxyuridine as a 1:1 mixture of two diastereomers. $[M+H]^+$ calculated for $C_{18}H_{19}ClFN_2O_8P$: 477.07; found: 477.0.

Example 4

(2R,3S,5R)-2-(((4-(3-Chlorophenyl)-2-oxido-1,3,2-dioxaphosphinan-2-yl)oxy)methyl)-5-(5-fluoro-2,4-dioxo-3,4-dihydropyrimidin-1(2H)-yl)tetrahydrofuran-3-yl pivalate (Compound 104)

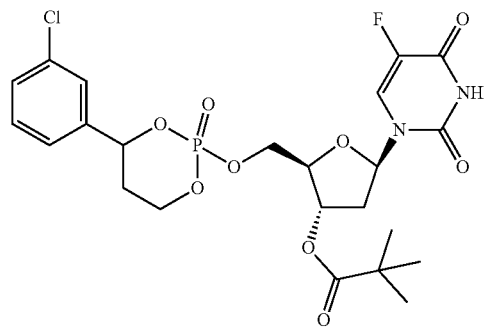 [SMILES: CC(C)(C)C(=O)O[C@H]1C[C@H](n2cc(F)c(=O)[nH]c2=O)O[C@@H]1COP1(=O)OCCC(c2cccc(Cl)c2)O1]

Compound 104 was prepared according to the method similar to that described in Example 1 from pivalic acid, 1-(3-chlorophenyl)-1,3-propanediol, and 5-fluoro-2'-deoxyuridine as a 1:1 mixture of two diastereomers. $[M-H]^+$ calculated for $C_{23}H_{27}ClFN_2O_9P$: 559.1; found: 559.0.

Biological Examples

Examples of use of the method include the following. It will be understood that the following are examples and that the method is not limited solely to these examples.

Example A: Tissue Distribution Following Oral Administration of Reference Compounds and the Disclosed Compounds The liver specificity of the disclosed compounds is compared relative to a corresponding active compound in liver and other organs that could be targets of toxicity.

Methods:

Reference compounds and the 5-fluorouridine monophosphate cyclic triester compounds are administered at 5-20 mg/kg to fasted rats by oral gavage. Plasma concentrations of the active, metabolite, and 5-fluorouridine monophosphate cyclic triester compounds in circulation and in the hepatic portal vein are determined by HPLC-UV, and the liver, small intestine, and other organ concentrations are measured by LC-MS using the standard chromatography method.

Results:

TABLE 1

Tissue distribution of active metabolites in rats at 1 and 5 hours after oral administration of the compounds at 5 mg/kg dose

| Compound | 101 | 103 | 104 | NUC-3373 |
|---|---|---|---|---|
| FdUMP$_{liver}$ at 1, 5 h (ng/g) | 135, 47.9 | 50.9, <18 | 108, 50.5 | 54.8, <18 |
| FUDR$_{blood}$ at 1, 5 h (ng/mL) | 9.9, <5 | <2, <2 | 3.96, <2 | 11.4, 3.5 |
| FdUMP$_{liver}$/FUDR$_{blood}$ at 1, 5 h | 13.6, >9.6 | >25, na | 27, >25 | 4.8, na |

FdUMP$_{liver}$-monophosphate liver level;
FUDR$_{blood}$-5-fluorouridine blood level;
na-not available The results of selected new compounds, which demonstrates the liver targeting of the 5-fluorouridine monophosphate cyclic triester compounds and provide evidence for improved efficiency of the compounds over other types of compounds in liver-targeting and achieving higher level of the active in the liver. This can occur solely by the high efficiency liver targeting provided by the 5-fluorouridine monophosphate cyclic triester compounds.

The results demonstrate higher 5-fluoro-2'-deoxyuridine monophosphate (FdUMP) levels in the liver and lower nucleotide level in blood than NUC-3373 that is a ProTide prodrug of the same nucleotide after oral administration of selected compounds at 5 mg/kg oral dose in rats.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15%, 10%, 5%, 3%, 1%, 0.1%, or otherwise. Similarly, in certain embodiments, the terms "generally perpendicular" and "substantially perpendicular" refer to a value, amount, or characteristic that departs from exactly perpendicular by less than or equal to 15%, 10%, 5%, 3%, 1%, 0.1%, or otherwise.

The above description discloses several methods and materials. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

Although the invention has been described with reference to embodiments and examples, it should be understood that numerous and various modifications can be made without departing from the spirit of the invention. Accordingly, the invention is limited only by the following claims.

What is claimed is:
1. A compound having the structure of Formula Ia or Ib:

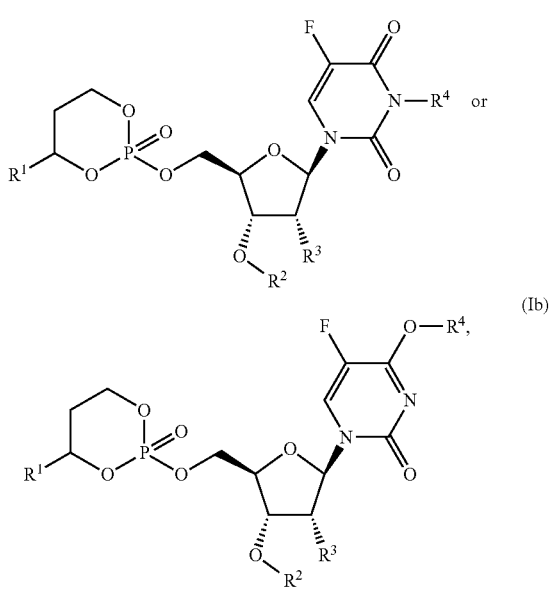

or a stereoisomer or a pharmaceutically acceptable salt thereof,
wherein:
$R^1$ is an optionally substituted aryl;
$R^2$ is selected from a group of H, an optionally substituted $C_1$-$C_{10}$ heteroalkyl, an optionally substituted $C_1$-$C_{10}$ acyl, an optionally substituted $C_1$-$C_{10}$ heteroacyl, an optionally substituted $C_1$-$C_{10}$ alkyl-C-carboxy, and an optionally substituted $C_1$-$C_{10}$ alkyl-C-amido;
$R^3$ is selected from a group of H, OH, and an optionally substituted $C_1$-$C_{10}$ acyloxy; and
$R^4$ is selected from a group of H, an optionally substituted $C_1$-$C_{10}$ heteroalkyl, and an optionally substituted $C_1$-$C_{10}$ acyl.

2. The compound of claim 1 having the structure of Formula Ia:

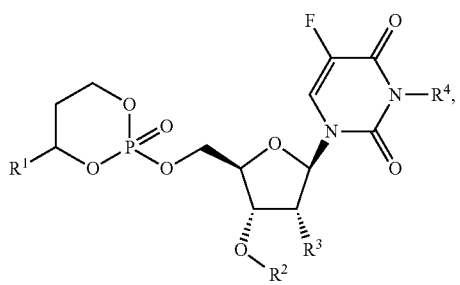

(Ia)

or a stereoisomer or a pharmaceutically acceptable salt thereof.

3. The compound of claim 1, wherein $R^1$ is 3-chlorophenyl.

4. The compound of claim 3, wherein $R^2$ is H, or an optionally substituted $C_1$-$C_{10}$ acyl.

5. The compound of claim 4, wherein $R^3$ is H.

6. The compound of claim 5, wherein $R^4$ is H.

7. The compound of claim 1, wherein $R^2$ is H, or an optionally substituted $C_1$-$C_{10}$ acyl.

8. The compound of claim 7, wherein $R^2$ is —C(=O)CH$_3$, —C(=O)CH$_2$CH$_3$, —C(=O)CH$_2$CH$_2$CH$_3$, —C(=O)CH(CH$_3$)$_2$ or —C(=O)C(CH$_3$)$_3$.

9. The compound of claim 1, wherein $R^3$ is H, or OH.

10. The compound of claim 9, wherein $R^3$ is H.

11. The compound of claim 1, wherein $R^4$ is H.

12. The compound of claim 1 having the structure of Formula Ib:

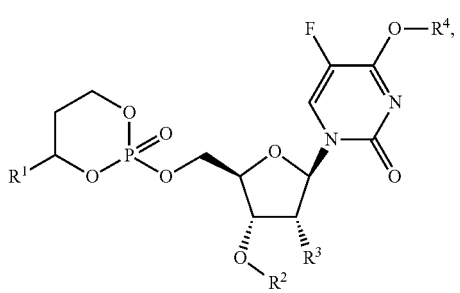

(Ib)

or a stereoisomer or a pharmaceutically acceptable salt thereof.

13. The compound of claim 12, wherein $R^1$ is substituted phenyl; $R^2$ is H, or an optionally substituted $C_1$-$C_{10}$ acyl; $R^3$ is H, or OH; and $R^4$ is H.

14. The compound of claim 1 selected from the group consisting of:

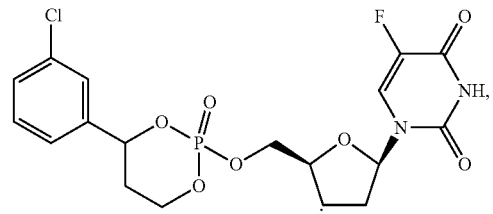

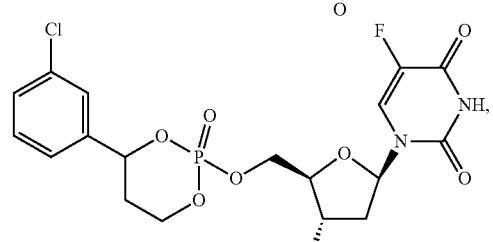

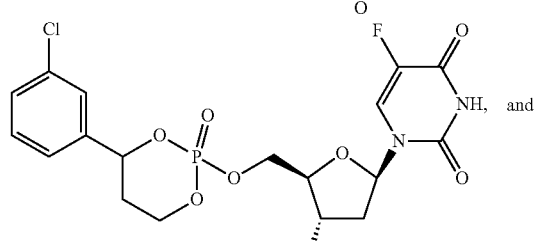

and

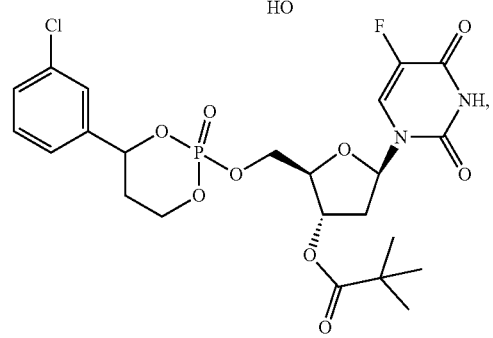

or a stereoisomer or a pharmaceutically acceptable salt thereof.

15. A pharmaceutical composition, comprising a compound of claim 1; and a pharmaceutically acceptable excipient.

16. A pharmaceutical composition, comprising a compound of claim 14; and a pharmaceutically acceptable excipient.

17. A method of treating hepatocellular carcinoma comprising administering an effective amount of a compound of claim 1.

18. A method of treating hepatocellular carcinoma comprising administering an effective amount of a compound of claim 14.

* * * * *